United States Patent
Cox et al.

(10) Patent No.: US 6,503,909 B1
(45) Date of Patent: Jan. 7, 2003

(54) PYRAZINE COMPOUNDS

(75) Inventors: Brian Cox, Stevenage (GB); Mark Patrick Healy, Cambridge (GB); Deborah Wild, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/762,295

(22) PCT Filed: Aug. 26, 1999

(86) PCT No.: PCT/EP99/06248

§ 371 (c)(1),
(2), (4) Date: Feb. 8, 2001

(87) PCT Pub. No.: WO00/12488

PCT Pub. Date: Mar. 9, 2000

(30) Foreign Application Priority Data

Aug. 28, 1998 (GB) ............................................... 9818881

(51) Int. Cl.⁷ ..................... A61K 31/4965; A61P 25/08; C07D 241/20; C07D 241/26
(52) U.S. Cl. .................................. 514/252.1; 544/407
(58) Field of Search ........................ 544/407; 514/252.1

(56) References Cited

U.S. PATENT DOCUMENTS

| 3,544,568 A | * 12/1970 | Cragoe et al. | ............... 544/407 |
|---|---|---|---|
| 3,575,975 A | 4/1971 | Cragoe | ........................ 260/250 |
| 4,402,958 A | 9/1983 | Izzo et al. | ................... 424/250 |

FOREIGN PATENT DOCUMENTS

WO    WO 98/38174 A1    9/1998

OTHER PUBLICATIONS

Ram Lakhan, Babban Ji Rai, "Novel Syntheses of Heterocycles from x–Oxonitriles; Part III. 2–Amino–3–arylpyrazines", Synthesis vol. 10, Oct. 1987, Stuttgart DE, 914–915—XP002069087.
Chemical Abstracts, vol. 97, No. 28, 1982, Columbus, Ohio, US, Abstract No. 110034z, p. 617 and JP 08238778A (Kyowa Gas Chem Ind) Mar. 3, 1982.

* cited by examiner

*Primary Examiner*—Richard L. Raymond
*Assistant Examiner*—Venkataraman Balasubramanian
(74) *Attorney, Agent, or Firm*—Bacon & Thomas

(57) ABSTRACT

A compound of formula (I) wherein $R^1$ is phenyl substituted by one or more halogen atoms; $R^2$ is —$NH_2$; $R^3$ is —$NH_2$ or hydrogen; $R^4$ is —$CXNR^aR^b$, —$CXNH$—$(CH_2)_y$—$NR^aR^b$; wherein X is =O or +S; y is an integer zero, 1 or 2; $R^a$ and $R^b$, which may be the same or different, are selected from hydrogen and $C_{1-4}$ alkyl or together with the nitrogen atom to which they are attached form a saturated 5- or 6-membered heterocycle containing one or two nitrogen heteroatoms, which heterocycle can be further substituted with one or more $C_{1-4}$ alkyl groups; and pharmaceutically acceptable derivatives thereof.

8 Claims, No Drawings

PYRAZINE COMPOUNDS

The present invention relates to a class of pyrazine compounds which are useful in the treatment of central nervous system (CNS) diseases and disorders and to their pharmaceutically acceptable derivatives, to pharmaceutical compositions containing them, to their use in the treatment of such disorders and to methods of preparation.

Numerous phenyl pyrazine derivatives are known in the prior art. For example, Synthesis (1987, (10), 914–915, describes phenyl pyrazine derivatives including, inter alia, 3-(4-chlorophenyl)pyrazinamine. No pharmaceutical utility is however described in that prior art document.

The present invention relates to pyrazine derivatives which are sodium channel blockers. The compounds are surprisingly potent anti-convulsants having increased potency with respect to lamotrigine and increased selectivity in terms of CNS side-effects and inhibition of the enzyme dihydrofolate reductase. The compounds are therefore useful in the treatment of CNS diseases such as epilepsy.

Accordingly, the present invention provides a compound of formula (I)

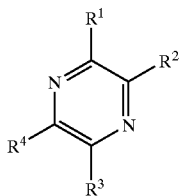

(I)

wherein
R$^1$ is phenyl substituted by one or more halogen atoms;
R$^2$ is —NH$_2$;
R$^3$ is —NH$_2$ or hydrogen;
R$^4$ is —CXNR$^a$R$^b$, —CXNH—(CH$_2$)$_y$—NR$^a$R$^b$;
wherein
X is =O or =S;
y is an integer zero, 1 or 2;
R$^a$ and R$^b$, which may be the same or different, are selected from hydrogen and C$_{1-4}$ alkyl, or together with the nitrogen atom to which they are attached, form a saturated 5- or 6-membered heterocycle containing one or two nitrogen heteroatoms, which heterocycle can be further substituted with one or more C,4 alkyl groups;
and pharmaceutically acceptable derivatives thereof.

By pharmaceutically acceptable derivative is meant any pharmaceutically acceptable salt, solvate or ester, or salt or solvate of such ester of the compounds of formula (I), or any other compound which upon administration to the recipient is capable of providing (directly or indirectly) a compound of formula (I) or an active metabolite or residue thereof (eg. a prodrug).

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts of the compounds of formula (I) include acid addition salts formed with inorganic or organic acids, preferably inorganic acids, e.g. hydrochlorides, hydrobromides and sulphates.

Suitable prodrugs are well-known in the art and include N-acyl derivatives, for example at any of the nitrogens in the compounds of formula (I), for example simple acyl derivatives such as acetyl, propionyl and the like or groups such as R—O—CH$_2$-nitrogen or R—O—C(O)-nitrogen.

As used herein, the term halogen atom includes fluorine, chlorine, bromine or iodine.

The term C$_{1-4}$alkyl as used herein includes straight chained and branched alkyl groups containing 1 to 4 carbon atoms, and in particular includes methyl and isopropyl.

The term saturated 5- or 6-membered heterocycle containing one or two nitrogen heteroatoms as used herein includes 5- or 6-membered heterocycles containing at least one nitrogen heteroatom, and preferably two nitrogen heteroatoms, which heterocycle can be further substituted with one or more C$_{1-4}$ alkyl groups. A particularly suitable heterocycle is a pyrrolidine or a piperazine ring.

R$^1$ is aptly selected from phenyl substituted by one or more halogen atoms. Particularly, R$^1$ represents phenyl substituted by more than 1 halogen atom, such as di- or tri-halogenated phenyl. Preferably, the halogen atoms are all identical. Preferably, the halogen substituents in R$^1$ are chloro. Suitably R$^1$ is selected from 2,3,5-trichlorophenyl, 2,3-dichlorophenyl, 2,5-dichlorophenyl. Preferably, R$^1$ is 2,3,5-trichlorophenyl.

R$^3$ is preferably —NH$_2$.

When R$^4$ is the group —CXNR$^a$R$^b$ or —CXNH—(CH$_2$)$_y$—NR$^a$R$^b$ where R$^a$ and R$^b$, together with the nitrogen atom to which they are attached, form a saturated 5- or 6-membered heterocycle containing one or two nitrogen heteroatoms atoms, this saturated 5- or 6-membered heterocycle is suitably a pyrrolidine or piperazine ring.

X is preferably =O.

The integer y is preferably 2.

When R$^4$ is the group —CXNH—(CH$_2$)$_y$—NR$^a$R$^b$, R$^a$ and R$^b$ are preferably C$_{1-4}$ alkyl. Preferred values for —CXNH(CH$_2$)$_y$NR$^a$R$^b$ include for example —CONH—(CH$_2$)$_2$—N(CH$_3$)$_2$.

R$^4$ is preferably the group —CXNR$^a$R$^b$. Preferably X is =O and, further preferred, are compounds where R$^a$ and R$^b$ are selected from hydrogen and C$_{1-4}$ alkyl. Preferably R$^4$ is —CONH$_2$, —CONH(CH$_3$), —CONH(CH$_2$CH$_3$), —CONH[CH(CH$_3$)$_2$] or —CON(CH$_3$)$_2$. A particularly preferred R$^4$ is —CONH$_2$.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Preferred compounds of the present invention include:
5-Carboxamido-2,6-diamino-3-(2,3,5-trichlorophenyl) pyrazine
2,6-Diamino-5-N-methylcarboxamido-3-(2,3,5-trichlorophenyl)pyrazine
2,6-Diamino-5-N-ethylcarboxamido-3-(2,3,5-trichlorophenyl )pyrazine
2,6-Diamino-5-N-isopropylcarboxamido-3-(2,3,5-trichlorophenyl)pyrazine
2,6-Diamino-5-N,N-dimethylcarboxamido-3-(2,3,5-trichlorophenyl)pyrazine
2,6-Diamino-5-thiocarboxamido-3-(2,3,5-trichlorophenyl)pyrazine
and pharmaceutically acceptable derivatives thereof.

A particularly preferred compound according to the invention is:
5-Carboxamido-2,6-diamino-3-(2,3,5-trichlorophenyl) pyrazine
and pharmaceutically acceptable derivatives thereof.

It is to be understood that the present invention covers all combinations of particular and preferred groups as described herein above.

The compounds of formula (I) are particularly useful as anticonvulsants. They are therefore useful in treating epilepsy. They may be used to improve the condition of a host, typically a human being, suffering from epilepsy. They may be employed to alleviate the symptoms of epilepsy in a host. "Epilepsy" is intended to include the following seizures:- simple partial seizures, complex partial seizures, secondary generalised seizures, generalised seizures including absence seizures, myoclonic seizures, clonic seizures, tonic seizures, tonic clonic seizures and atonic seizures.

The compounds of formula (I) are additionally useful in the treatment of bipolar disorder, alternatively known as manic depression. Type I or II bipolar disorder may be treated. The compounds of formula (I) may thus be used to improve the condition of a human patient suffering from bipolar disorder. They may be used to alleviate the symptoms of bipolar disorder in a host. The compounds of formula (I) may also be used in the treatment of unipolar depression.

The compounds of formula (I) are also useful as analgesics. They are therefore useful in treating or preventing pain. They may be used to improve the condition of a host, typically a human being, suffering from pain. They may be employed to alleviate pain in a host. Thus, the compounds of formula (I) may be used as a pre-emptive analgesic to treat acute pain such as musculoskeletal pain, post operative pain and surgical pain, chronic pain such as chronic inflammatory pain (e.g. rheumatoid arthritis and osteoarthritis), neuropathic pain (e.g. post herpetic neuralgia, trigeminal neuralgia and sympathetically maintained pain) and pain associated with cancer and fibromyalgia. The compounds of formula (I) may also be used in the treatment or prevention of pain associated with migraine.

The compounds of formula (I) are further useful in the treatment of functional bowel disorders which include non-ulcer dyspepsia, non-cardiac chest pain and in particular irritable bowel syndrome. Irritable bowel syndrome is a gastrointestinal disorder characterised by the presence of abdominal pain and altered bowel habits without any evidence of organic disease. The compounds of formula (I) may thus be used to alleviate pain associated with irritable bowel syndrome. The condition of a human patient suffering from irritable bowel syndrome may thus be improved.

The compounds of formula (I) may also be useful in the treatment of neurodegenerative diseases, such as Alzheimer's disease, ALS, motor neuron disease, Parkinson's disease, macular degeneration and glaucoma. The compounds of formula (I) may also be useful in neuroprotection and in the treatment of neurodegeneration following stroke, cardiac arrest, pulmonary bypass, traumatic brain injury, spinal cord injury or the like.

The compounds of formula (I) are further useful in the treatment of tinnitus.

Still further, the compounds of formula (I) are also useful in preventing or reducing dependence on, or preventing or reducing tolerance or reverse tolerance to, a dependence-inducing agent. Examples of dependence inducing agents include opioids (eg morphine), CNS depressants (eg ethanol), psychostimulants (eg cocaine) and nicotine.

According to a further aspect of the invention, we provide a compound of formula (I) or a pharmaceutically acceptable derivative thereof for use in human or veterinary medicine.

According to another aspect of the invention, we provide use of a compound of formula (I) or a pharmaceutically acceptable derivative thereof in the manufacture of a medicament for use in the treatment of a disorder substantially as hereinbefore described.

According to a further aspect of the invention, we provide a method of treating a human or animal subject suffering from, or susceptible to, a disorder substantially as hereinbefore described, which method comprises administering to said subject a therapeutically effective amount of a compound of formula (I) or a pharmaceutically acceptable derivative thereof.

It is to be understood that reference to treatment as used herein includes treatment of established symptoms and prophylactic treatment, unless explicitly stated otherwise.

The compound of formula (I) and its salts may be administered orally at a dose of from 0.1 to 10 mg/kg body weight per day and more particularly 0.3 to 3 mg/kg body weight per day, calculated as the free base. The dose range for adult human beings is generally from 8 to 1000 mg/day, such as from 35 to 800 mg/day, preferably 20 to 200 mg/day, calculated as the free base.

The precise amount of the compounds of formula (I) administered to a host, particularly a human patient, will be the responsibility of the attendant physician.

However, the dose employed will depend upon a number of factors including the age and sex of the patient, the precise condition being treated and its severity, and the route of administration.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

While it is possible for the compounds of formula (I) or a pharmaceutically acceptable derivative thereof to be administered as the raw chemical, it is preferable to present it as a pharmaceutical formulation. The formulations of the present invention comprise the compounds of formula (I) or a pharmaceutically acceptable derivative thereof together with one or more acceptable carriers or diluents therefor and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compound of formula (I) or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The compounds of formula (I) may be used in combination with other therapeutic agents, for example other anticonvulsants. When compounds of formula (I) or pharmaceutically acceptable derivatives thereof are used in combination with other therapeutic agents, the compounds may be administered either sequentially or simultaneously by any convenient route. The invention thus provides, in a further aspect, a combination comprising a compound of formula (I) or a pharmaceutically acceptable derivative thereof with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease, the dose of each compound may differ from that when the compound is used alone. Appropriate doses will be readily appreciated by those skilled in the art.

Preferred unit dosage formulations are those containing an effective daily dose, as herein above recited, or an appropriate fraction thereof, of the active ingredient. Conveniently that may be from 5 mg to 1000 mg, such as from 8 mg to 1000 mg, more conveniently 35 mg to 800 mg, and most conveniently 20 to 200 mg, calculated as the free base.

The present invention provides a process for preparing compounds of formula (I) and pharmaceutically acceptable derivatives thereof.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof are described below and which form a further aspect of the invention. In the formulae that follow, $R^1$ to $R^4$ are as defined in formula (I) above unless otherwise stated. According to a first process (A), compounds of formula (I) may be prepared by interconversion, utilising other compounds of formula (I) as precursors.

Thus, compounds of formula (I) wherein X is S may be prepared from the corresponding compound of formula (I) wherein X is O, by treatment with a thiation agent, preferably Lawessons reagent. Conveniently, the reaction is effected in the presence of a solvent or solvents, such as a halogenated hydrocarbon (e.g. dichloromethane) and/or toluene and at elevated temperature, for example 100° C.

According to another process (B), compounds of formula (I), where $R^4$ is —$CONH_2$, may be prepared from a compound of formula (II)

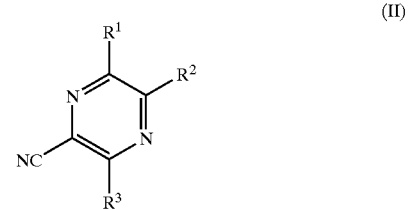

(II)

by hydrolysis under suitable reaction conditions and according to conventional procedures, eg. using sulphuric acid.

According to another process (C), compounds of formula (I) where X is O may be prepared under suitable reaction conditions by reacting a compound of formula (III)

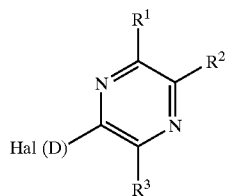

(III)

or a protected derivative thereof, where Hal (D) represents a halogen atom, suitably bromine, with a palladium catalyst, preferably palladium (II) acetate, a ferrocene, preferably bis(diphenylphosphino)ferrocene and an amine, in the presence of carbon monoxide. The reaction is carried out in a solvent, such as dimethylformamide and at elevated temperature, for example between 65° C. and 125° C.

Compounds of formula (II) may be prepared by reacting compounds of formula (III) or a protected derivative thereof, where Hal (D) represents a halogen atom, suitably bromine, with a cyanating agent preferably with a mixture of sodium cyanide and copper (I) cyanide. The reaction is carried out in a solvent, such as dimethylformamide and at elevated temperature, for example 130° C.

Compounds of formula (III) may be prepared by reacting compounds of formula (IV)

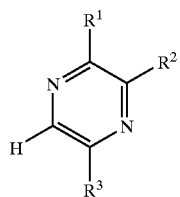

(IV)

or a protected derivative thereof with a suitable halogenating agent, for example N-bromosuccinimide. The reaction is conveniently carried out in a suitable solvent, such as dimethylsulfoxide and below room temperature, for example 15° C.

Compounds of formula (IV) where $R^2$ represents $NH_2$ may be prepared by cyclisation and oxidation of a compound of formula (V)

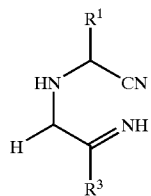

(V)

or a salt thereof according to conventional procedures, for example by neutralising a salt of a compound of formula (V), e.g. with lithium hydroxide in a suitable solvent such as an alcohol, e.g. methanol, under which conditions spontaneous oxidation to a compound of formula (IV) occurs.

Compounds of formula (V) may be prepared by reacting compounds of formula (VI) $R^1C(O)H$ with compounds of formula (VII) $R^3$

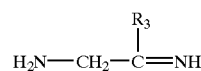

or a salt thereof, in the presence of a cyanide source, for example potassium cyanide. Compounds of formula (VI), where $R^1$ is trihalo-substituted phenyl, for example 2,3,5-trichlorobenzaldehyde, are known and may be prepared according to the methods described in WO95/07877. Compounds where $R^1$ represents alternative values are either known or may be prepared according to methods known for the preparation of known compounds.

Compounds of formula (VII), for example aminoacetamidine, may be prepared according to known procedures, for example, those described in Chem. Berichte, 89, 1185 (1956).

Compounds of formula (IV) may also be prepared from compounds of formula (VII)

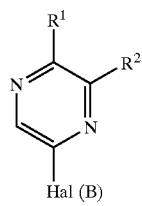

(VIII)

or a protected derivative thereof where Hal (B) represents a halogen atom, suitably chloride. For example, Hal(B) may be converted to —$NR^bR^c$ by reaction with an appropriate amine in a solvent, such as ethanol and at elevated temperature, for example 180° C.

A compound of formula (VIII) may suitably be prepared from a compound of formula (IX)

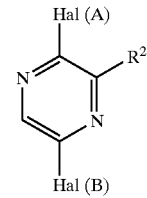

(IX)

or a protected derivative thereof by reaction with a compound of formula (X) $R^1B(OH)_2$ in the presence of a palladium catalyst, preferably tetrakis(triphenylphospine) palladium(0). Examples of compounds of formula (X) $R^1B(OH)_2$ include 2,3,5-trichlorobenzeneboronic acid, 2,3-dichlorobenzeneboronic acid and 2,5-dichlorobenzeneboronic acid. Appropriately, Hal(A) in above formula (IX) is more reactive than Hal(B), and suitably Hal(A) is selected from bromide and iodide, whereas Hal(B) is aptly chloride. Compounds of formula (X) are either commercially available or can suitably be prepared from commercially available benzene analogues e.g. 1-bromo-2,3-dichlorobenzene or 2-bromo-4,6-dichloroaniline as described hereinafter in greater detail in the accompanying Examples.

A compound of formula (IX) can be suitably prepared by further halogenating a compound of formula (XI)

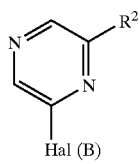

(XI)

or a protected derivative thereof for example by reaction with a halogenating agent, such as N-bromosuccinimide, with stirring at below room temperature, for example between −5° C. and 0° C., for several hours.

A compound of formula (XI) can be prepared from a di-halo compound of formula (XII)

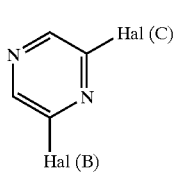

(XII)

by reaction with $R^2H$, where Hal(B) and Hal(C) may be the same or different halogen substituents. Aptly both Hal(B) and Hal(C) are chloride. Compounds of formula (XII) are commercially available. The reaction is carried out at elevated temperature, for example 150° C.

Certain intermediates described above are novel compounds, and it is to be understood that all novel intermediates herein form further aspects of the present invention.

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The following Examples which should not be construed as constituting a limitation thereto are provided to illustrate the invention.

INTERMEDIATE 1

2,3,5-Trichlorobromobenzene

Sodium nitrite (3.88 g, 0.056 mole) was added in portions to concentrated sulphuric acid (28.16 ml) stirred below 10° C. A solution of 2-bromo-4,6-dichloroaniline (12 g, 0.05 mole, Lancaster) in glacial acetic acid (126 ml) was added maintaining the temperature below 10° C. The mixture was stirred below 10° C. for 1 hr and then slowly added to a stirred solution of cuprous chloride (10.11 g, 0.10 mole) in concentrated hydrochloric acid (101.05 ml) at room temperature. The mixture was then stirred at room temperature for 17 hrs. The product was filtered, washed with water (3×50 ml), dissolved in chloroform (150 ml), dried over anhydrous magnesium sulphate, filtered and the filtrate evaporated in vacuo to give the desired product. Yield 10 g (77%), M.p. 55–57° C.

INTERMEDIATE 2

2,3,5-Trichlorobenzeneboronic Acid

A solution of 2,3,5-trichlorobromobenzene (8.60 g, 0.033 mole) in dry ether (33 ml) and bromoethane (4.73 ml, 7.31 g, 0.067 mole) was added dropwise to a suspension of magnesium turnings (2.80 g, 0.12 mole) in dry ether (21.50 ml) at room temperature. The mixture was refluxed for 0.50 hr and cooled to room temperature. The mixture was then added dropwise under nitrogen to a solution of trimethylborate (5.16 ml, 5.16 g, 0.05 mole) in dry ether (8.60 ml) maintaining the temperature below −60° C. This was warmed to room temperature overnight, then cooled in an ice-bath and treated with 2M hydrochloric acid (10 ml). The ether layer was separated, washed with water (2×20 ml), dried over anhydrous magnesium sulphate, filtered and the filtrate evaporated in vacuo. The residue was triturated with 40–60° C. petroleum ether, filtered and dried in vacuo. Yield 4.57 g (61%), M.p. 257–260° C.

INTERMEDIATE 3

2-Chloro-6-amino-pyrazine

A suspension of 2,6-dichloropyrazine (100 g, 0.67 mole, Lancaster) in 0.880 ammonia (500 ml) was stirred and heated at 150° C. in a glass lined autoclave at 20 atm for 16 hrs. The cooled mixture was filtered, washed well with water (200 ml) and dried. The product was recrystallised from chloroform. Yield 41.98 g (48%), M.p. 150–152° C.

INTERMEDIATE 4

2-Chloro-3-bromo-6-aminopyrazine and 2-amino-3-bromo-6-chloropyrazine

A solution of 2-chloro-6-aminopyrazine (20 g, 0.15 mole) in chloroform (1940 ml) was stirred at −5° C. to 0° C. N-Bromosuccinimide (27.58 g, 0.15 mole) was added in portions maintaining the temperature between −5 and 0° C. The mixture was warmed to room temperature and stirred for 3.50 hrs. The mixture was then washed with aqueous saturated sodium bicarbonate (1×300 ml), then water (1×500 ml), dried over anhydrous magnesium sulphate, filtered and the filtrate evaporated down in vacuo. The residue was purified by 'flash chromatography' using chloroform as the eluent. Yield of 2-chloro-3-bromo-6-aminopyrazine 13.89 g (43%), M.p. 146–147° C. Yield of 2-amino-3-bromo-6-chloropyrazine 4.90 g (15%), M.p. 124–125° C.

INTERMEDIATE 5

2-Amino-6-chloro-3-(2,3,5-trichlorophenyl)pyrazine

A solution of 2,3,5-trichlorobenzeneboronic acid (1.62 g, $7.18 \times 10^{-3}$ mole) in absolute ethanol (2.05 ml) was added slowly to a mixture of 2-amino-3-bromo-6-chloropyrazine (1 g, $5.1 \times 10^{-3}$ mole) and tetrakis(triphenylphospine)palladium(0) (0.334 g, $2.89 \times 1^{-4}$ mole) in benzene (10.20 ml)/2M aqueous sodium carbonate (5.50 ml). The mixture was refluxed for 17 hrs. The cooled reaction mixture was evaporated in vacuo and then extracted with chloroform (50 ml). The chloroform layer was washed with water (2×30 ml), dried over anhydrous magnesium sulphate, filtered and the filtrate evaporated down in vacuo. The residue was triturated with 40–60° C. petroleum ether, filtered and dried in vacuo. Yield 0.205 g (14%), M.p. 211–214° C.

INTERMEDIATE 6

2-{[Cyano-(2,3,5-trichlorophenyl)-methyl]-amino}-acetamidine Hydrobromide

Aminoacetamidine dihydrobromide (162.1 g, 0.774 mole) was added in portions to a solution of 2,3,5- trichlorobenzaldehyde (200.0 g, 0.851 mole) in methanol (2.43 litres) at room temperature. Once the addition was complete potassium cyanide (50.4 g, 0.774 mole) was added in one portion to the resulting mixture. The suspension was then stirred at 25° C. for 4 hours before being warmed to 50° C. The mixture is stirred at 50° C. for 24 hours. Methanol was then removed in vacuo, the resulting solid was slurried in water (1.5 litres) and ethyl acetate (2.5 litres) and collected by filtration. The solid was then dried in vacuo at 50° C. overnight to give the desired product. Yield 96.31 g (33.4%), $^1$H nmr (d-6 DMSO) δ/ppm 8.72 (3H, br, NH); 7.99 (1H, d, J 2.3 Hz, ArH); 7.79 (1H, d, J 2.3 Hz, ArH); 5.39 (1H, d, J 10.6 Hz, ArCH(CN)NH); 4.35 (1H, m, ArCH(CN) NH); 3.56 (2H, d, J 6.4 Hz, ArCH(CN)NHCH$_2$C(=NH) NH$_2$).

INTERMEDIATE 7

2,6-Diamino-3-(2,3,5-trichlorophenyl)pyrazine

2-{[Cyano-(2,3,5-trichlorophenyl)-methyl]-amino}-acetamidine hydrobromide (95.36 g, 0.256 mole) was added in portions to a solution of lithium hydroxide monohydrate (16.11 g, 0.384 mole) in methanol (1.9 litres) at room temperature. The resulting solution was stirred at room temperature for 3 hours before being evaporated to dryness in vacuo. The resulting solid was slurried in water (1.15 litres) and collected by filtration. After drying at 50° C. in vacuo the crude material was purified by recrystallisation from toluene to give the desired product. Yield 69.51 g (93.8%), M.p. 178–180° C.

A suspension of 2-amino-6-chloro-3-(2,3,5-trichlorophenyl)pyrazine (0.3 g, 9.71×10$^{-4}$ mole) in absolute ethanol (4 ml) and 0.880 aqueous ammonia (8.24 ml) was stirred and heated in an autoclave at 180° C. for 44 hrs. The cooled mixture was evaporated in vacuo, and the residue extracted with chloroform (3×30 ml). The combined chloroform extracts were dried over anhydrous magnesium sulphate, filtered and the filtrate evaporated down in vacuo. The residue was purified by 'flash chromatography' using chloroform to 98:2 chloroform:methanol as the eluent. The product was triturated with 40–60° C. petroleum ether, filtered and dried in vacuo. Yield 0.155 g (56%), M.p. 178–180° C.

INTERMEDIATE 8

5-Bromo-2,6-Diamino-3-(2,3,5-trichlorophenyl) pyrazine

N-Bromosuccinimide (0.194 g, 1.09×10$^3$ mole) was added over 20 min to a mixture of 2,6-diamino-3-(2,3,5-trichlorophenyl)pyrazine (0.3 g, 1.04×10$^{-3}$ mole) in dimethylsulfoxide (10 ml) and water (0.25 ml) below 15° C. The resulting reaction mixture was stirred at 15° C. for 1 hr, poured onto ice water (150 ml) and extracted with ethyl acetate (2×75 ml). The extract was then washed with 2 M sodium carbonate solution (50 ml) and water (100 ml), dried over anhydrous magnesium sulphate, filtered and the filtrate evaporated in vacuo. The residue was purified by 'flash chromatography' using 5–13% ethyl acetate in cyclohexane as the eluent. Yield 0.183 g (48%), M.p. 222–224° C.

INTERMEDIATE 9

5-Cyano-2,6-Diamino-3-(2,3,5-trichlorophenyl) pyrazine

A mixture of 97% sodium cyanide (0.064 g, 1.306×10$^{-3}$ mole) and 90% copper(I) cyanide (0.135 g, 1.306×10$^{-3}$ mole) in dry dimethylformamide (5 ml) was stirred and heated to 130° C. To the resulting clear solution was added 5-Bromo-2,6-Diamino-3-(2,3,5-trichlorophenyl)pyrazine (0.35 g, 0.95×10$^{-3}$ mole) in small portions, and the solution was maintained at 140–150° C. for 16 hrs. The reaction mixture was cooled and evaporated in vacuo. The residue was extracted with ethyl acetate (100 ml), washed with water (100 ml) and brine (100 ml), dried over anhydrous magnesium sulphate, filtered and the filtrate evaporated in vacuo. The residue was purified by 'flash chromatography' using 5–17% ethyl acetate in cyclohexane as the eluent. Yield 0.152 g (51 %), M.p. 277–279° C.

EXAMPLE 1

5-Carboxamido-2,6-Diamino-3-(2,3,5-trichlorophenyl)pyrazine

5-Cyano-2,6-Diamino-3-(2,3,5-trichlorophenyl)pyrazine (0.1 g, 3.18×10$^{-4}$ mole) was dissolved in 75% sulphuric acid (8 ml) and heated to 90° C. for 20 min. The reaction was then cooled to 0° C. and basified (dropwise) with 2 M sodium hydroxide solution. The yellow suspension was extracted with ethyl acetate (100 ml), washed with brine (50 ml), dried over anhydrous magnesium sulphate, filtered and the filtrate evaporated in vacuo. The residue was purified by 'flash chromatography' using 9–27% ethyl acetate in cyclohexane as the eluent. Yield 0.079 g (75%), M.p. 245–247° C. Anal. Calcd for C$_{11}$H$_8$N$_5$C$_3$O: C, 39.73; H, 2.42; N, 21.06. Found: C, 39.88; H, 2.13; N, 20.53.

EXAMPLE 2

2,6-Diamino-5-N-Methylcarboxamido-3-(2,3,5-Trichlorophenyl)pyrazine

5-Bromo-2,6-diamino-3-(2,3,5-trichlorophenyl)pyrazine (0.5 g, 1.36×10$^{-3}$ mol), palladium(II)acetate (10.×10$^{-2}$ g, 4.45×10$^{-5}$ mol, 3 mol %), and bis(diphenylphosphino) ferrocene (2.3×10$^{-2}$ g, 4.1 5×10$^{-5}$ mol, 3 mol %) were all added to dimethylformamide (5 ml). Carbon monoxide gas and methylamine gas were continually bubbled through the solution whilst heating at 70° C., for 6 hours. The mixture was cooled, poured into water (50 ml), extracted with ethyl acetate (3×30 ml). The organics were combined and washed with 10% aq. citric acid solution (2×20 ml), brine (20 ml), dried over anhydrous magnesium sulfate, filtered and the filtrate evaporated in vacuo. Purification was by 'flash chromatography' using 50% cyclohexane/ethyl acetate as the eluent. Yield 0.078 g (16.6%), Anal. Calcd. for C$_{12}$H$_{10}$N$_5$Cl$_3$O: C, 41.56: H, 2.89; N, 20.20. Found: C, 41.42; H, 2.64; N, 19.87. N.m.r.(CDCl$_3$) δ ppm: 2.91+2.92 (3H, 2×s), 7.34(1H, d), 7.49(1H, s broad), 7.57(1H, d).

EXAMPLE 3

2,6-Diamino-5-N-Ethylcarboxamido-3-(2,3,5-Trichlorophenyl)pyrazine

5-Bromo-2,6-diamino-3-(2,3,5-trichlorophenyl)pyrazine (0.5 g, 1.36×10$^{-3}$ mol), palladium(II)acetate (3.0×10$^{-2}$ g, 1.36×10$^{-4}$ mol, 10 mol %), bis(diphenylphosphino) ferrocene (7.5×10$^{-2}$ g, 1.36×10$^{-4}$ mol, 10 mol %), and 2M ethylamine in tetrahydrofuran (9 ml, 1.8×10$^{-2}$, 13 eq) were all added to dimethylformamide (50 ml). Carbon monoxide gas was bubbled through the mixture for 10 minutes which was then heated at 100° C., for 4 hours. The mixture was cooled, volatiles removed in vacuo, and the brown oil partitioned between water and diethyl ether. Aqueous was re-extracted with diethyl ether (×2). The organics were combined, filtered through a pad of J2 harborlite, washed with 10% aq. citric acid solution, brine, dried over anhydrous magnesium sulfate, filtered and the filtrate evaporated in vacuo. Purification was by 'flash chromatography' using 1:1 cyclohexane/ethyl acetate as the eluent. Yield 0.048 g (9.8%), N.m.r.(CDCl$_3$) δ ppm: 1.22(3H, t), 3.41(2H, m), 4.60(2H, broad s), 7.35(1H, d), 7.42(1H, s broad), 7.57(1H, d). LC/MS EI M$^+$=360/362.

EXAMPLE 4

2,6-Diamino-5-N-isopropylcarboxamido-3-(2,3,5-Trichlorophenyl)pyrazine

5-Bromo-2,6-diamino-3-(2,3,5-trichlorophenyl)pyrazine (0.5 g, 1.36×10$^{-3}$ mol), palladium(II)acetate (3.0×10$^{-2}$ g, 1.36×10$^{-4}$ mol, 10 mol %), bis(diphenylphosphino)ferrocene (7.5×10$^{-2}$ g, 1.36×10$^{-4}$ mol, 10 mol %), and isopropylamine (5 ml, 5.9×10$^{-2}$, 43 eq) were all added to dimethylformamide (50 ml) in an autoclave. Carbon monoxide gas was bubbled through the mixture for 10 minutes, the autoclave was then seated and heated at 120° C., for 4 hours. The mixture was cooled, more palladium(II)acetate (3.0×10$^{-2}$ g, 1.36×10$^{-4}$ mol, 10 mol %), bis(diphenylphosphino)ferrocene (7.5×10$^{-2}$ g, 1.36×10$^{-4}$ mol, 10 mol %) and isopropylamine (4 ml, 4.7×10$^{-2}$, 34.5 eq) were added and more carbon monoxide gas was bubbled through the mixture for a further 10 minutes. The autoclave was then sealed and heated at 120° C., for a further 4 hours. The mixture was then cooled, volatiles removed in vacuo, and the brown oil partitioned between water and diethyl ether. Aqueous was re-extracted with diethyl ether (×2). The organics were combined, filtered through a pad of J2 harborlite, washed with 10% aq. citric acid solution, brine, dried over anhydrous magnesium sulfate, filtered and the filtrate evaporated in vacuo. Purification was by 'flash chromatography' using 1:1 cyclohexane/ethyl acetate as the eluent. Yield 0.098 g (19.3%), N.m.r.(CDCl$_3$) δ ppm: 1.23 (6H, d), 4.16(1H, m), 4.59(2H, broad s), 7.24(1H, broad s), 7.34(1H, d), 7.57(1H, d). LC/MS EI M$^+$=374/376.

EXAMPLE 5

2,6-Diamino-5-N,N-Dimethylcarboxamido-3-(2,3,5-Trichlorophenyl)pyrazine

5-Bromo-2,6diamino-3-(2,3,5-trichlorophenyl)pyrazine (0.5 g, 1.36×10$^{-3}$ mol), palladium(II)acetate (2.3×10$^{-2}$ g, 1.02×10$^{-4}$ mol, 7.6 mol %) and bis(diphenylphosphino)ferrocene (4.6×10$^{-2}$ g, 8.30×10$^{-5}$ mol, 6.1 mol %) were all added to dimethylformamide (50 ml). Carbon monoxide gas was bubbled through for 10 minutes and then methylamine gas was continually bubbled through the solution whilst heating at 70° C., for 4.5 hours. The mixture was cooled, more palladium(II)acetate (2.3×10$^{-2}$ g, 1.02×10$^{-4}$ mol, 7.6 mol %) and bis(diphenylphosphino)ferrocene (4.6×10$^{-2}$ g, 8.30×10$^{-5}$ mol, 6.1 mol %) were added and more carbon monoxide gas was bubbled through the mixture for a further 10 minutes. Methylamine gas was continually bubbled through the solution whilst heating at 70° C., for a further 3 hours. The mixture was cooled, more palladium(II)acetate (2.3×10$^{-2}$ g, 1.02×10$^{-4}$ mol, 7.6 mol %) and bis(diphenylphosphino)ferrocene (4.6×10$^{-2}$ g, 8.30×10$^{-5}$ mol, 6.1 mol %) were added and more carbon monoxide gas was bubbled through the mixture for a further 10 minutes. Methylamine gas was continually bubbled through the solution whilst heating at 70° C., for a further 2.5 hours. The mixture was then cooled, volatiles removed in vacuo, and the brown oil partitioned between water and ethyl acetate. Aqueous was re-extracted with ethyl acetate(×2). The organics were combined, washed with 10% aq. citric acid solution, brine, dried over anhydrous magnesium sulfate, filtered and the filtrate evaporated in vacuo. Purification was by 'flash chromatography' using 2:1–1:1 cyclohexane/ethyl acetate as the eluent. Yield 0.061 g (12.5%), N.m.r.(CDCl$_3$) δ ppm: 3.07+3.24(2×3H, 2×s), 4.45(2H, broad s), 6.06(2H, broad s), 7.30(1H, d), 7.54(1H, d). LC/MS EI M$^+$=360/362.

EXAMPLE 6

2,6-Diamino-5-Thiocarboxamido-3-(2,3,5-trichlorophenyl)pyrazine

5-Carboxamido-2,6-diamino-3-(2,3,5-trichlorophenyl)pyrazine, (0.05 g, 1.50×10$^{-4}$ mole) was dissolved in toluene (20 ml) and dichloromethane (5 ml). Lawessons reagent (0.061 g, 1.50×10$^{-4}$ mole) was added and the reaction stirred at 100° C. under nitrogen for 16 hrs. A further three equivalents of Lawessons reagent (0.183 g) was then added and the reaction was stirred for a further six hours. The reaction mixture was cooled and evaporated in vacuo. The residue was purified by 'flash chromatography' using 5–22% ethyl acetate in cyclohexane as the eluent. Yield 0.0099 (17%)

Mass Spec: (electrospray) 350 (MH$^+$)

Retention Time 3.23 minutes

Micromass Platform Series 2

5 min Grad. (2mmABZ)

Instrument: Red Flow rate: 0.8 ml/min

Eluents: A—0.1%V/V Formic Acid+10 mmol Ammonium Acetate
B—95% MeCN+0.05% V/V Formic Acid Column: 5 cm×2.1 mm ID ABZ+PLUS Inject Vol: 5 µl Temp: RT

| Time | A% | B% |
|---|---|---|
| 0.00 | 100 | 0 |
| 3.50 | 0.0 | 100 |
| 5.00 | 0.0 | 100 |
| 5.50 | 100 | 0 |

PHARMACY EXAMPLES

Sterile Formulations

Example A

|  | mg/ml |
|---|---|
| Compound of the Invention | 0.1 mg |
| Sodium Chloride USP | 9.0 mg |
| Water for Injection USP qs to | 1 ml |

The components are dissolved in a portion of the water for injections and the solution made up to a final volume to provide 0.1 mg/ml of the compound of the Invention. Where a salt of the compound is used the quantity of compound is increased to provide 0.1 mg/ml of the free base. The solution may be packaged for injection, for example by filling and sealing into ampoules, vials or syringes. These may be aseptically filled and/or terminally sterilised by, for example, autoclaving at 121° C.

Further sterile formulations may be prepared in a similar manner to obtain alternative concentrations of the compound.

Example B

|  | mg/ml |
| --- | --- |
| Compound of the Invention | 0.5 mg |
| Mannitol | 50.0 mg |
| Water for Injections qs to | 1.0 ml |

Dissolve the components in a portion of the Water for Injections. Make up to final volume and mix until homogeneous. Filter formulation through a sterilising filter and fill into glass vials. Lyophilise and seal vials. Reconstitute with appropriate solvent prior to use.

Formulations for Oral Administration

Tablets may be prepared by the normal methods such as direct compression or wet granulation. The tablets may be film coated with suitable film forming materials, such as an Opadry, using standard techniques. Alternatively the tablets may be sugar coated.

Example C
Direct Compression Tablet

|  | mg/Tablet |
| --- | --- |
| Compound of the Invention | 5.0 mg |
| Magnesium Stearate | 4.0 mg |
| Microcrystalline Cellulose (Avicel PH102) qs to | 400.0 mg |

The compound of the Invention is passed through a 30 mesh sieve and blended with the Avicel and Magnesium Stearate. The resultant blend is compressed into tablets using a suitable tablet press fitted with 11.0 mm diameter punches so as to provide 5 mg of the Compound of the Invention per tablet. Tablets of other strengths, containing for example 25 or 100 mg /tablet of the Compound of the Invention may be prepared in a similar manner.

Example D
Wet Granulation Tablet

|  | mg/Tablet |
| --- | --- |
| Compound of the Invention | 5.0 mg |
| Pregelled Starch | 28.0 mg |
| Sodium Starch Glycollate | 16.0 mg |
| Magnesium Stearate | 4.0 mg |
| Lactose qs | 400.0 mg |

The Compound of the Invention, Lactose, Pregelled Starch and Sodium Starch Glycollate is dry mixed and then granulated using a suitable volume of Purified Water. The resultant granules are dried and then blended with the Magnesium Stearate. The dried granules are compressed using a suitable tablet press fitted with 11.0 mm diameter punches so as to provide 5 mg of the Compound of the Invention per tablet.

Tablets of other strengths such as 25 and 100 mg/tablet may be prepared.

Example E
Hard Gelatin Capsule

|  | mg/capsule |
| --- | --- |
| Compound of the Invention | 5.0 mg |
| Microcrystalline Cellulose (Avicel PH102) qs | 700.0 mg |

The Compound of the Invention is passed through a 30 mesh sieve and then blended with the Microcrystalline Cellulose to provide an homogeneous blend.

The blend may then be filled into size 0EL hard gelatin capsule shells so as to provide capsules containing 5.0 mg/capsule of Compound of the Invention. Alternative strengths such as 25 or 100 mg/capsule of Compound of the Invention may be made in a similar manner.

Example F
Soft Gelatin Capsule

|  | mg/capsule |
| --- | --- |
| Compound of the Invention | 10.0 mg |
| Polyethylene Glycol | 90.0 mg |
| Propylene Glycol qs | 200.0 mg |

Blend together the Polyethylene Glycol and Propylene Glycol using heat as necessary. Stir until homogeneous. Add the Compound of the Invention and mix until homogeneous. Fill into an appropriate gelatin mass to give soft gelatin capsules containing 200 mg of the formulation, to provide 10.0 mg /capsule of the Compound of the Invention.

Alternative strengths, for example, 5 and 25 mg/capsule of the Compound of the Invention may be prepared in a similar manner.

Example G
Syrup

|  |  |
| --- | --- |
| Compound of the Invention | 5.0 mg |
| Sorbitol Solution | 1500.0 mg |
| Glycerol | 1000.0 mg |
| Sodium Benzoate | 5.0 mg |
| Flavour | 12.5 mg |
| Purified Water qs to | 5.0 ml |

The Sodium Benzoate is dissolved in a portion of the purified water and the Sorbitol Solution added. The Compound of the Invention, Flavour and Glycerol are added and mixed until homogeneous. The resultant mixture is made up to volume with the purified water.

Other Formulations

Example H

Suppository

|  | mg/suppository |
| --- | --- |
| Compound of the Invention | 10.0 mg |
| Witepsol W32, hard fat qs | 2000.0 mg |

Melt the Witepsol W32 at approximately 36° C. To a portion of this add the Compound of the Invention and blend . Incorporate the remaining melted Witepsol W32 and blend until homogeneous. Fill mould with 2000 mg of the formulation to provide 10.0 mg /suppository of the Compound of the Invention.

Example 1

Transdermal

| Compound of the Invention | 5.0 mg |
| --- | --- |
| Silicone Fluid | 90.9 mg |
| Colloidal Silicone Dioxide | 5.0 mg |

Mix the silicone fluid and active together and add the colloidal silicone dioxide. The material is then dosed into a subsequently heat sealed polymeric laminate comprised of the following: polyester release liner, skin contact adhesive composed of silicone or acrylic polymers, a control membrane which is a polyolefin (foe example polyethylene or polyvinyl acetate) or polyurethane, and an impermeable backing membrane of a polyester multilaminate.

Biological Data

Anticonvulsant activity

A compound of formula (I) has been shown to have anti-epileptic activity in a rodent model of generalised epilepsy, the rat maximal electroshock test (MES) which is an animal model that reflects human generalised tonic-clonic seizures.

For example, male Han Wistar rats (150–200 grms) were dosed i.p. with a suspension of the test compound in 0.25% methylcellulose 2 hr prior to test. A visual observation was carried out just prior to testing for the presence of ataxia. Using auricular electrodes a current of 200 mA, duration 300 millisec, was applied and the presence or absence of hind limb extension noted. A compound of formula (I) exhibited an $ED_{50}$ of 1.4 mg/kg compared to 6.1 mg/kg for lamotrigine with a therapeutic index (ratio of the ataxia $ED_{50}$ and MES $ED_{50}$) of 21.6 compared to 3.3 for lamotrigine.

No apparent adverse or toxic effects were observed during the above in vivo test due to the administration of the compounds of the invention.

What is claimed is:

1. A method of treating a human or animal subject suffering from, or susceptible to, epilepsy, which method comprises administering to said subject a therapeutically effective amount of a compound of formula (I)

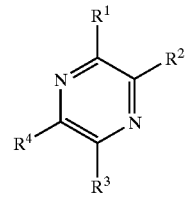

(I)

wherein $R^1$ is phenyl substituted by one or more halogen atoms;

$R_2$ is —$NH_2$;

$R_3$ is —$NH_2$ or hydrogen;

$R^4$ is —CXN $R^a$ $R^b$, —CXNH—$(CH_2)_y$N $R^a$ $R^b$;

wherein

X is =O or =S;

y is an integer zero, 1 or 2;

$R^a$ and $R^b$, which may be the same or different, are selected from the group consisting of hydrogen and $C_{1-4}$ alkyl, or together with the nitrogen atom to which they are attached, form a saturated 5- or 6-membered heterocycle containing one or two nitrogen heteroatoms, which heterocycle can be further substituted with one or more $C_{1-4}$ alkyl groups;

or a pharmaceutically acceptable salt or solvate thereof.

2. A method of treating a human or animal subject according to claim 1, wherein $R^1$ is 2,3,5-trichlorophenyl.

3. A method of treating a human or animal subject according to claim 1, wherein $R^3$ is —$NH_2$.

4. A method of treating a human or animal subject according to claim 2, wherein $R^3$ is —$NH_2$.

5. A method of treating a human or animal subject according to claim 1, wherein $R^4$ is —$CONH_2$.

6. A method of treating a human or animal subject according to claim 2, wherein $R^4$ is —$CONH_2$.

7. A method of treating a human or animal subject according to claim 3, wherein $R^4$ is —$CONH_2$.

8. A method of treating a human or animal subject according to claim 4, wherein $R^4$ is —$CONH_2$.

* * * * *